United States Patent [19]
Ardizio et al.

[11] Patent Number: 5,951,290
[45] Date of Patent: Sep. 14, 1999

[54] PROCEDURE FOR THE PREPARATION OF FIXED DENTAL PROSTHESES MADE OF RESIN, INSERTS FOR THE SAME AND FIXED PROSTHESES OBTAINED IN THIS WAY

[76] Inventors: Luigi Ardizio, Corso Risorgimento 121, 1-28100 Novara; Franco Ardizio, Via Cesare Pavesi 8B, 1-28062 Cameri (NO), both of Italy

[21] Appl. No.: 09/063,057

[22] Filed: Apr. 21, 1998

[30] Foreign Application Priority Data

Oct. 15, 1997 [IT] Italy ................................ CO97A0015

[51] Int. Cl.⁶ ...................................................... A61C 11/00
[52] U.S. Cl. ............................................ 433/213; 433/214
[58] Field of Search .................................... 433/213, 214, 433/191, 192, 193, 218, 219, 34

[56] References Cited

U.S. PATENT DOCUMENTS 4,609,351   9/1986   Blair ........................................... 433/55
4,705,476  11/1987   Blair ......................................... 433/171

FOREIGN PATENT DOCUMENTS 18 13 332   6/1970   Germany .
19 63 257   6/1971   Germany .

*Primary Examiner*—John J. Wilson
*Attorney, Agent, or Firm*—Young & Thompson

[57] ABSTRACT

Procedure for the production of fixed temporary and permanent dental prostheses made of resin, using preformed mastication inserts which are applied in a freely orientatable way to models and which are fixed thereto through the application of a little wax and which then have their cores completed with further wax. In making the baseplates the shaped mastication inserts remain first anchored in the baseplates and then in the resin forming the prosthesis. Manufacturing times for prostheses are drastically reduced and no special modeling ability is required from the dental technician. Using "twin prostheses" of the temporary prostheses, an "individual guide" for the construction of permanent prostheses made of resin, composite resin, ceramic or the like is obtained.

10 Claims, 10 Drawing Sheets

(Prior Art)

(Prior Art)

(Prior Art)

(Prior Art)

PROCEDURE FOR THE PREPARATION OF FIXED DENTAL PROSTHESES MADE OF RESIN, INSERTS FOR THE SAME AND FIXED PROSTHESES OBTAINED IN THIS WAY

FIELD OF THE INVENTION

This invention relates to a procedure for the preparation of fixed dental prostheses made of resin, inserts therefor and fixed prostheses so obtained.

BACKGROUND OF THE INVENTION

Until a few years ago fixed temporary dental prostheses were not widely used because, among other things, of their limited life (from a few months to some 1–1.5 years), their relatively high cost and the fact that generally they were intended for a mainly aesthetic purpose.

Recently in the field of dental treatment the real and specific positive functions of fixed temporary prostheses have been increasingly emphasized and reassessed, namely:

their therapeutic function, which among other things permits satisfactory conservation of the tissues and protection of the pulp from the thermal, chemical and bacterial points of view, the mechanical function, which among other things permits correctly balanced occlusion, restoration of the vertical dimension, correct intercuspation for satisfactory mastication, mandibular glide, compensation for any deformities, and so on, the aesthetic function, which at the same time results in correct morphology, correct phonology and improved hygiene.

Although fixed temporary and permanent prostheses according to the invention can be provided either as individual prostheses or comprising one or more adjacent teeth, or as two or more prostheses provided on one or both of the dental arches, in the description which follows and in the claims reference will be made to a case with several prostheses for greater clarity. Obviously it is to be understood that the teaching of this invention is independent of the number or type of prostheses produced at any time.

Hereinafter is depicted the known procedure for the production of temporary resin prostheses and permanent prostheses of hard material, or resin, composite resin, ceramic or the like.

The steps in question, substantially and in summary form, are as follows:

1) The dental practitioner (dentist) takes the necessary impressions from the patient, which will subsequently be used by the dental technician (dental mechanic) to prepare the temporary fixed prostheses made of resin.

2) Starting from the impressions received from the dental practitioner, the dental technician produces a model of the upper dental arch and a model of the lower dental arch in plaster (FIG. 1), positions the two models on the articulator (FIG. 2), and finds the correct position for movement and mastication, the occlusion relation and so on of the two models using the records of occlusion provided by the dental practitioner.

3) The dental practitioner and the dental technician study the correct positioning of the models in the articulator and draw the normal clinical conclusions from the points of view of dental treatment and technology.

4) Bearing in mind the general clinical assessments made in step 3), the dental technician relies on his experience and skill in three-dimensional modeling to first obtain the temporary fixed prostheses made of wax. For this purpose the dental technician starts by melting small quantities of wax (as in the so-called drop by drop technique) onto the corresponding model, and more specifically into the hollow areas of the dental arches in which the individual artificial teeth are to be positioned. In this the dental technician proceeds by gradually adding droplets of wax and modeling the individual teeth with a view to completing all the teeth which have to be reconstructed as required from time to time. Fixed temporary prostheses made completely of wax (FIG. 3, seen from above on the mastication side of models with wax teeth in contrasting color; FIG. 4, models with fixed temporary prostheses of wax in the closed position) are obtained in this way. It is obvious that the quality of the shaping of the wax teeth will depend strictly on the personal modeling skill of the dental technician, and in all cases will require extensive modeling time.

5) After the modeling has been carried out and the various parameters which have to be considered have been checked, the dental technician prepares the baseplates, and more specifically one baseplate for each future temporary prosthesis. The baseplates are prepared by applying a mass of plaster or silicone to the wax teeth (FIG. 5).

6) After removing the wax from the model and from the baseplates with jets of hot water, the baseplates and the associated models represent the "negative" of the wax teeth, or a "mold" with cavities (FIG. 6), the shape of which corresponds to the shape of the previously modeled wax teeth, from which the teeth previously made of wax will be obtained in resin. For this purpose the dental technician carries out the so-called "wedging" of the baseplates with resin, or fills the cavities in the baseplates with resin, and then subsequently brings about polymerization of the resin, e.g. by stoving.

7) When polymerization is complete, after the baseplates have been removed from the resin prostheses obtained on the models and these have been positioned in the articulator, the dental technician carries out the steps of checking, rough shaping, finishing and polishing the temporary fixed prostheses. When these operations are complete the temporary prostheses are delivered to the dental practitioner.

8) The dental practitioner places each of the temporary prostheses in the patient's mouth and checks that all functions and predetermined objectives are fulfilled. If this is the case he then fixes the temporary prostheses temporarily using conventional adhesives. If necessary the dental practitioner may make small changes, e.g. by grinding.

It will be seen that the making of teeth by diagnostic modeling in wax constitutes the most difficult and delicate step for the dental technician, who must rely on his skill and mastery as a "sculptor", on the one hand conceiving of the work of sculpting the finished teeth, and then on the other hand putting it into practice by modeling, creating shapes compatible with their corresponding contexts, or guaranteeing optimum mastication. Dental technicians therefore currently need to be well endowed with manual skill and imagination to find and achieve by modeling a proper balance between aesthetic shape, function, optimum mastication and the solution of individual problems. It is obvious that the search for this balance requires both high creative ability—a rare and valuable gift, not always naturally endowed—and a considerable expenditure of time in the daily practice of modeling. This results in quite high costs for the preparation of temporary fixed prostheses.

It will also be noted that once the time specified for use of the temporary prostheses has passed, the final fixed prostheses must be produced in hard material, e.g. resin, composite resin, ceramic, etc., incorporating the corresponding metal or fiber reinforcements. The dental practitioner will again take impressions from the patient's mouth, after having removed the temporary prostheses, so that the dental technician can prepare the permanent fixed prostheses. It is therefore obvious that preparation of the permanent fixed prostheses will be carried out again using the procedure mentioned above. This obviously results in a similar expense in terms of time and cost.

SUMMARY OF THE INVENTION

The main object, therefore, of the invention is to provide a procedure for the production of fixed dental prostheses of the type indicated in the introduction which avoids the disadvantages of the known art, which makes it possible to produce temporary and permanent fixed prostheses with teeth modeled in an optimum way and with an irreproachable masticatory engagement between the upper and the lower teeth, in a drastically shortened time, and this without in practice requiring any special modeling skill on the part of the dental technician.

An important aspect of this invention in the scope of the main object indicated above is to be seen in the fact of providing a procedure capable of offering a reliable "individual, or individual patient, guide" for the preparation of the subsequent permanent fixed prostheses to ensure an optimum conformation for the permanent prostheses from the outset, using some of the steps in the procedure for the production of the temporary prostheses, with only virtually negligible additional expense, all likewise bringing about a drastic reduction in production times without requiring any special skill on the part of the dental technician.

In the concept of the invention a parallel object is to be seen in the fact of providing preformed mastication inserts for teeth which make it possible to achieve the drastic reduction in tooth modeling time mentioned and to provide an immediate check on both vertical and horizontal spaces while the temporary prostheses are being created. With respect to the preformed inserts a further purpose of the invention comprises the fact of providing retaining means for the preformed inserts which ensure that they are correctly positioned in the baseplates while the temporary prostheses are being produced, and also providing incorporated retaining means on the so-called "individual guide" in the preparation of permanent prostheses.

The objects of the invention in relation to the procedure and the preformed inserts are accomplished by means of the features indicated herein.

The procedure for the production of fixed temporary dental prostheses made of resin may include the following steps, which are in part known:

1) formation of the models: from the impressions provided by the dental practitioner the dental technician obtains the upper model and the lower model in a known way, that is working models, where, if the subsequent preparation of permanent fixed prostheses is envisaged, the dental technician also produces a duplicate of the working models and then positions the two pairs of models (the working and the duplicate models) each in an articulator, 2) investigation of the models—clinical assessment: the dental technician and the dental practitioner investigate the models in the articulators in a known way and draw clinical conclusions from the points of view of dental treatment and technology, 3) diagnostic fitting of the preformed inserts: in the light of the investigation of the models and the clinical assessments in step 2), the dental technician selects the most suitable preformed inserts from a plurality of preformed mastication inserts of modular teeth which are available to him, and following the application of a few drops of wax to the individual working models fixes the inserts, one for each tooth, into the models with a few drops of wax. Having then assessed the harmony of the shapes of the inserts on the model and the normal diagnostic parameters, the dental technician easily completes the lingual or palatal cervical zones of the shaped teeth, 4) preparation of the baseplates and formation of temporary prostheses and "twin" prostheses: the dental technician now obtains the baseplates for the temporary prostheses in a known way by applying a suitable mass of e.g. silicone or wax to the teeth created on the models, formed of a preformed mastication insert and an internal part or body of wax respectively, 5) wedging with resin and its polymerization: if it is also intended to subsequently prepare permanent fixed prostheses, the dental technician, using the same baseplates, carries out two wedging operations, that is filling of the baseplates with resin, with corresponding polymerization of the resins, and more specifically first on the working models (to obtain the temporary prostheses) and then on the duplicate models (to obtain the "twin" prostheses), 6) checking and finishing: once the resin has been polymerized, the prostheses obtained, that is the temporary prostheses and the "twin" prostheses, are checked and finished in a known way, the temporary prostheses being completed by polishing, 7) fitting the temporary prostheses to the patient: the dental practitioner inserts the temporary prostheses into the patient's mouth in a known way and checks that all functions are satisfactory, in which case he cements the temporary prostheses temporarily, 8) removal of the temporary prostheses and preparation of impressions for fixed permanent prostheses: after the dental practitioner has established that the patient is suitable for the fitting of permanent fixed prostheses, he removes the temporary prostheses from the patient and determines the impressions and the mastication; at this step the "twin" prostheses are used in order to obtain the impressions, and, filled with impression material, are themselves inserted into the patient's mouth and used for recording the mastication, the laterals, masticatory functions and the permanent impression, to which the dental practitioner makes any necessary corrections by grinding or adding material, 9) having received the impressions from the dental practitioner, the dental technician develops them by obtaining new models for the permanent prostheses, these models comprising the "twin" prostheses inserted in the models, which are then mounted in the articulator, and the retaining means are removed, 10) new baseplates are prepared without removing the "twin" prostheses from the new models, 11) the permanent fixed prostheses are then obtained from the new baseplates using the known steps for their preparation, whereupon the permanent fixed prostheses are fixed in the patient's mouth by the dental practitioner.

Also, in accordance with the invention, through use of the impressions taken from the patient using the "twin" prostheses, crowns and metal structures, for example of gold, or similar components, can also be obtained from the baseplates then obtained.

According to the invention the preshaped mastication inserts are distinguished by the fact that they individually comprise a body of resin or the like, in the case of temporary prostheses, or of composite resin, ceramic or other hard materials in the case of permanent prostheses, comprising a cusped mastication surface and a profiled sleeve provided for each type of tooth in a plurality of sizes and cusp shapes, so as to take into account the different sizes of teeth existing in nature and so as to form a modular series of preshaped inserts from which the most suitable insert for a particular case can be rapidly found as required, with an immediate check on both vertical and horizontal spaces during the production of a dental prosthesis.

The preformed inserts are characterized in that they are obtained by suitable techniques, for example molding with a male and female die, in which the outer surface is obtained smooth and the inner surface is preferably rough and the body obtained is substantially transparent.

The preformed inserts are characterized in that they are provided with integral or removable external retaining means, for example in the form of pins or bosses, suitable for creating an anchorage for an individual preformed insert in the base plate during the step in which the wax is removed.

The "twin" prostheses have external integral retention means obtained directly during the second wedging of the baseplates used to obtain the temporary prostheses in the first wedging (step 5).

The preformed inserts are characterized in that the profiling of the inserts relates either to the variable thickness along the perimeter of the sleeve of the inserts or the free edge of the sleeve, where the perimeter line of the free edge of the said sleeve matches the shape of the patient's gums, and the maximum height of the sleeve is in any event such as to ensure free orientation of the mastication or the insert in space so as to permit a perfect masticatory matching between the teeth in the prosthesis and the corresponding upper or lower teeth.

The mastication inserts may present a coloring which reproduces the teeth natural coloring, that is the mastication inserts present colored veins at the valley-bottoms in the mastication surface. The dental prostheses according to the present invention look, therefore, like natural teeth of the prostheses holder.

In order to facilitate the production of the mastication inserts, the latter may also be manufactured as one-piece groups of two or more mastication inserts. Alternatively, the insert groups can also consist of two or more mastication inserts which are fixed together by adhesives or the like.

The advantages which are achieved through the invention mainly comprise the fact that with the availability of the preformed mastication inserts mentioned, available as a plurality of modular teeth, virtually no special modeling skill on the part of the dental technician is required any more; he merely has to choose the preformed tooth mastication insert which is most appropriate and orientate it correctly in order to obtain irreproachable mastication, and to complete the bodies of the individual teeth with wax and model them, in which this latter modeling is well known to be extremely simple, and can be carried out by any dental technician without any difficulty.

As a consequence of the use of the preformed mastication inserts mentioned, the time for the preparation of prostheses can be drastically reduced in that all the time required for the very difficult modeling currently necessary for the cusp mastication surfaces of the teeth is omitted. The two aspects mentioned above also include a substantial reduction in the cost of preparing prostheses. Another advantage of the invention lies in the fact that with adoption of the proposed preformed inserts it is easily possible to obtain an immediate check on both vertical and horizontal spaces when producing prostheses, which likewise contributes to a drastic reduction in preparation time. A further advantage will be seen in that by providing preformed inserts of an enamel mass or using substantially transparent bodies it is possible to immediately effect correct positioning and/or retouching of the inserts because it is possible to observe the underlying zone or area. By providing a variable thickness for the sleeve the correct chromatic appearance of the teeth in temporary fixed prostheses can be reproduced in a very natural way. The natural appearance can also be improved providing the above mentioned colored veins. Another advantage of the invention is that the procedure and the mastication inserts proposed can form prostheses independently of the shape of the interdental spaces which have to be filled, that is the prostheses obtained can allow without distinction for the presence of tooth stumps, metal fittings or inserts in the jawbones, actual cavities and so on. Also, in the case of prostheses comprising several consecutive teeth, with the preformed inserts and the proposed procedure it is also possible to produce directly prostheses incorporating metal or fiber reinforcement. Although enamel mass of type S15= Biodent K+B Plus (Biodent is a registered trade mark of the company DE TREY of Wiesbaden, Germany) is indicated as a material for forming mastication inserts for temporary prostheses, it is understood that they can also be prepared using any other suitable material.

Another important advantage of the invention lies in the fact that in the proposed procedure provision is also made, in addition to the easier preparation of temporary fixed prostheses, for duplicate or "twin" prostheses which are used for taking impressions for the permanent fixed prostheses by the dental practitioner, and for recording mastication, laterals and masticatory functions, and therefore serve effectively as an "individual guide" for preparation of the permanent fixed prostheses by means of an extremely simplified, shortened and therefore more economical procedure. The fact that the permanent prostheses obtained according to the invention have an effectively definitive individual conformation, that of the patient, or only require very minor retouching, is also of advantage. Furthermore, through the use of these "twin" prostheses it is also possible to obtain baseplates, crowns and metal structures, for example of gold, more easily using known techniques.

A further advantage lies in the fact that the mastication inserts can be held in position either in an incorporated way in the course of preparation or in the form of removable bodies which can be secured for example by adhesive bonding. A further important advantage lies in the fact that "twin" prostheses, copies of the temporary prostheses, can easily be produced by simply using the duplicate copies of the upper and/or lower models, which are original like the baseplates used to obtain the temporary prostheses. The need to make a copy of the original or working models is due to the fact that during the procedure to obtain temporary prostheses the working models may suffer breakage or modifications which are not actually present in the patient's mouth.

Yet another major advantage of the invention lies in the fact that providing preformed mastication inserts of hard material, as permanent inserts, for example of composite resin or ceramic, and placing these in the base of the baseplates for the permanent prostheses, on the one hand ensures that there is the desired thickness of dental enamel and on the other hand makes it easier to prepare the bodies of the teeth, for example by laying up ceramic.

Further objects, features, advantages and details of the procedures for the preparation of temporary and/or permanent fixed prostheses and preformed mastication inserts according to the invention will be apparent subsequently from the following detailed description taken in connection with the accompanying drawings.

BRIEF DESCRIPTION OF THE DRAWINGS

The features of this invention which are believed to be novel are set forth with particularity in the following description and in the appended claims. The invention, together with its objects and the advantages thereof, may be best understood by reference to the following description provided purely by way of a non-restrictive example with reference to the drawings which show respectively in perspective:

FIG. 15 shows a single mastication insert and a group of four mastication inserts, respectively.

DETAILED DESCRIPTION OF THE PREFERRED EMBODIMENTS

In the following description of both the known procedure and the procedure according to the invention for the production of temporary fixed prostheses or subsequently advantageously also permanent prostheses, the same reference numbers, supplemented by a letter when they refer to this invention, are used for identical parts or components in the various figures. In the case considered provision is made for the production of four prostheses, more specifically two in the upper dental arch and two in the lower dental arch. For greater ease of understanding the working wax has been selected to be of a color which contrasts with the whitish color of the models.

Figure 1:
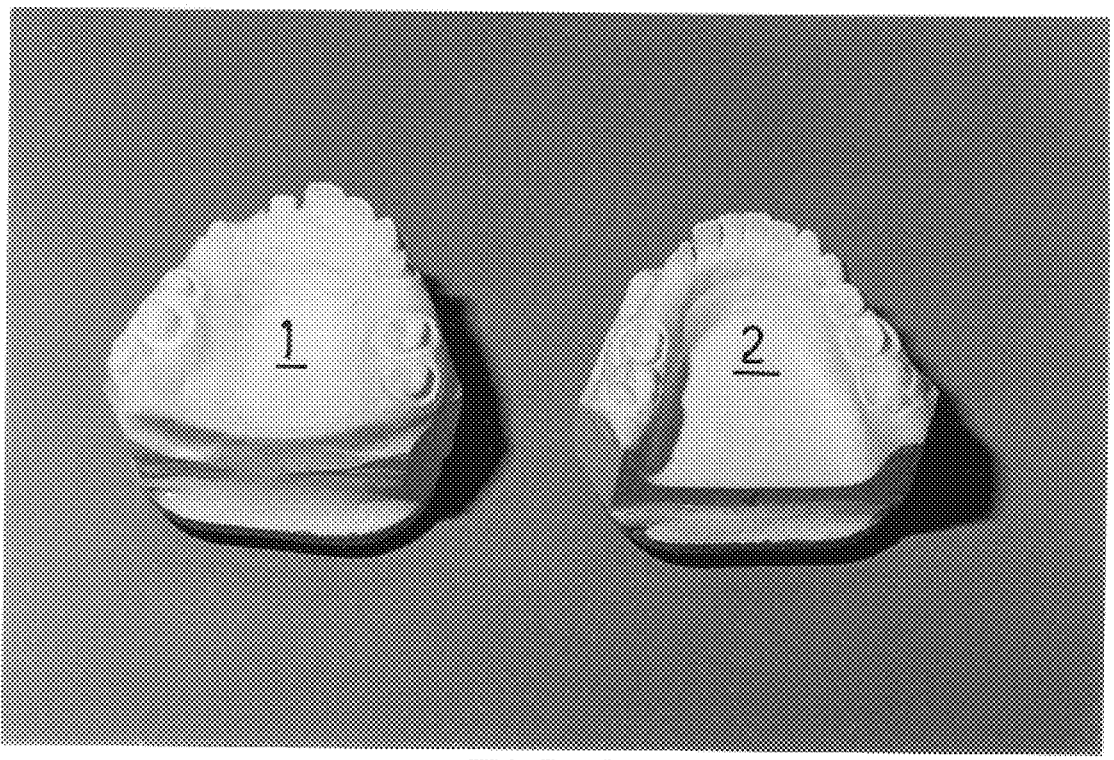
FIGS. 1 to 7 show the known technique for the production of fixed temporary or subsequently permanent prostheses.
Figure 2:
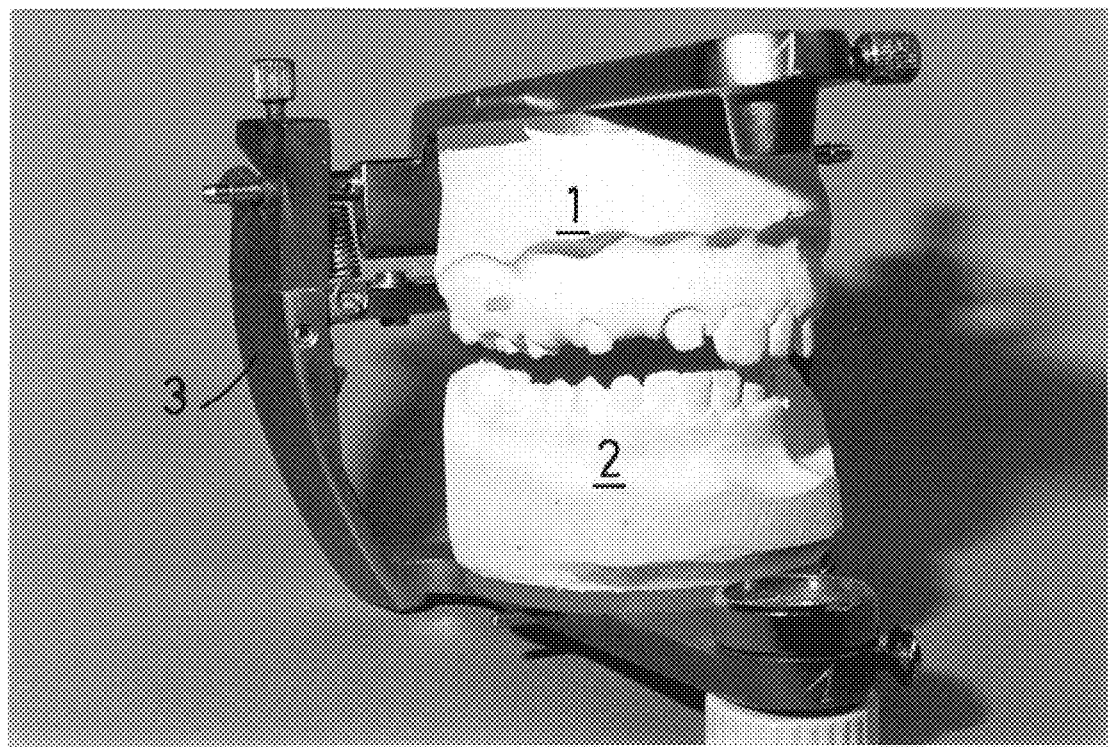

Known art:

As described in the introduction, starting from the impressions provided by the dental practitioner, the dental technician prepares models for the upper dental arch 1 and the lower dental arch 2 (FIG. 1) and positions the models 1 and 2 on articulator 3 (FIG. 2).

Figure 3:
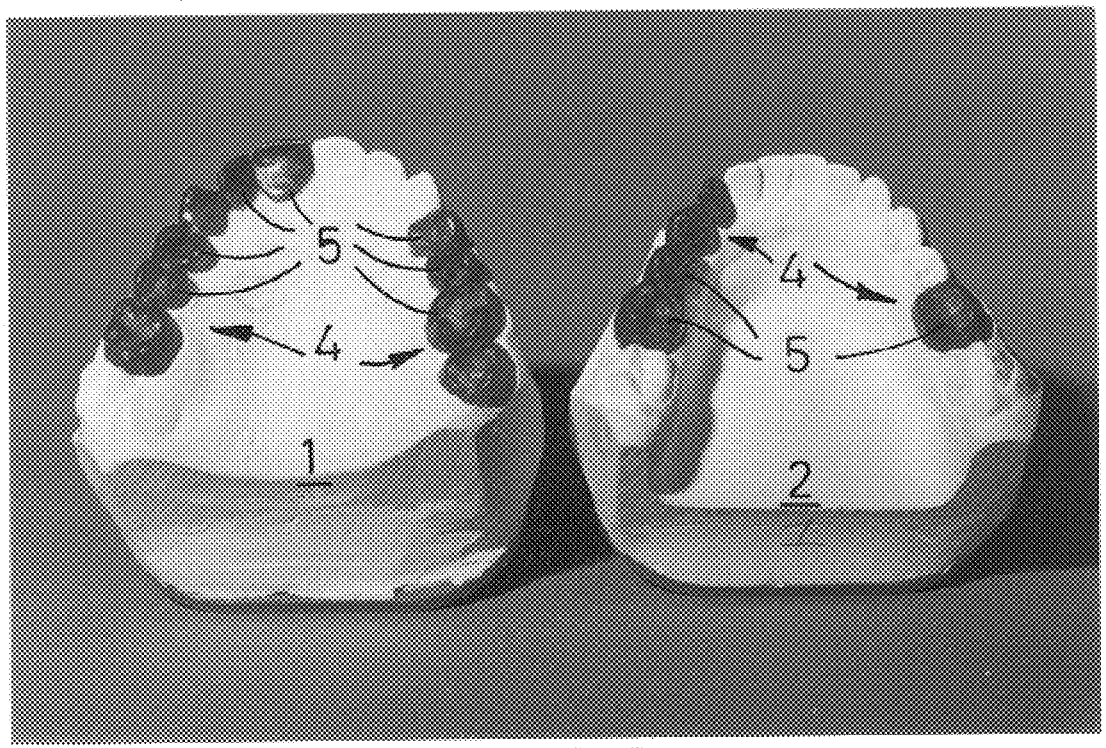
Figure 4:
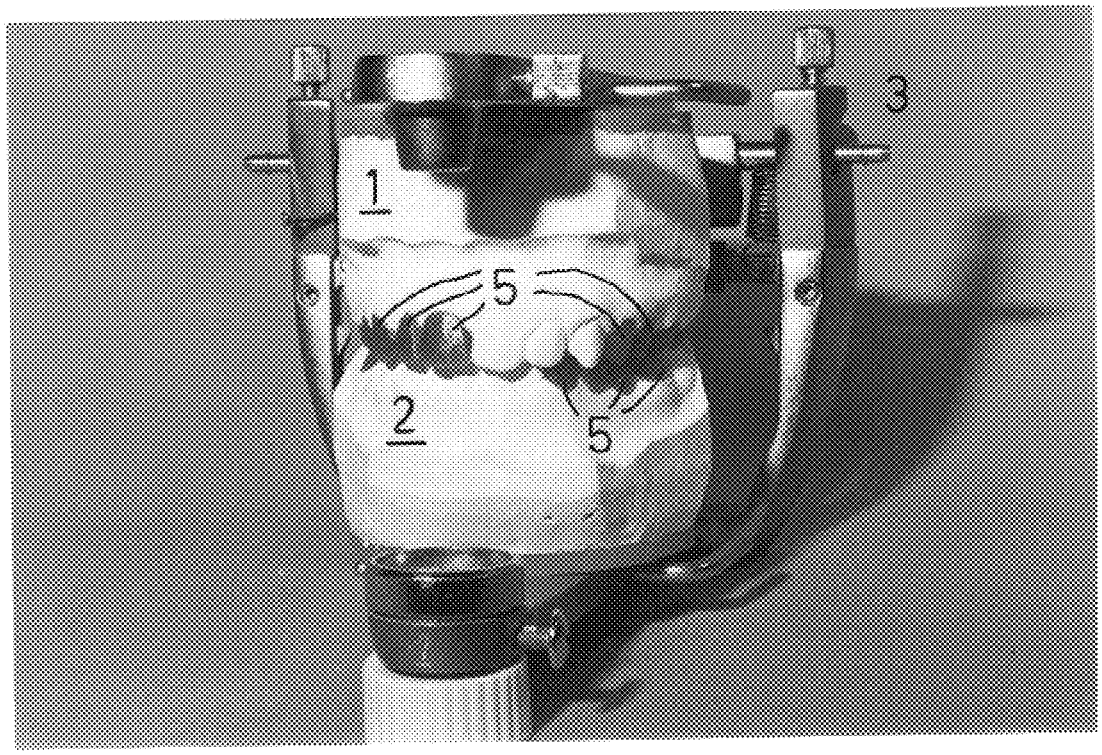

After investigating the models in the articulator and making the normal clinical assessments from the point of view of dental treatment and dental technology, the dental technician carries out diagnostic waxing up, starting by melting small quantities of wax drop by drop which he positions on the model, and making use of his experience and skill in modeling or sculpting forms in space begins and continues with modeling of the individual teeth which have to be reconstructed until the temporary fixed prostheses are completely created in wax, in the case in question the four fixed prostheses 4, in which the individual wax teeth are indicated by 5 (FIGS. 3 and 4).

Figure 5:
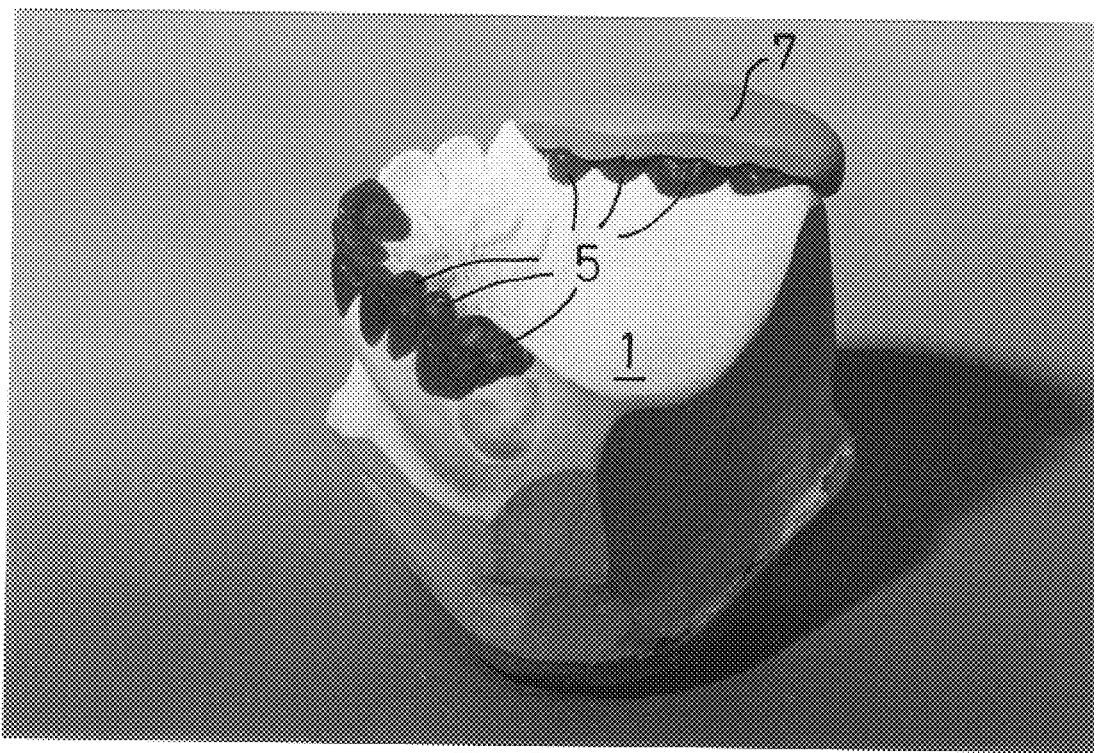
Figure 6:
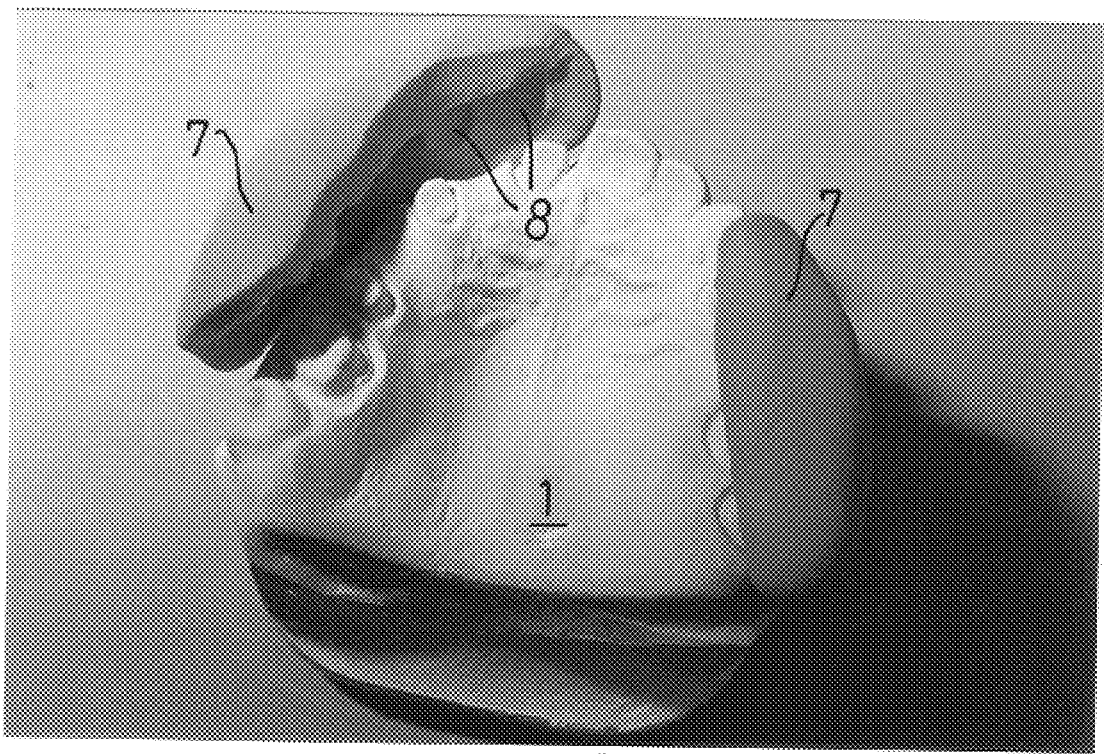

After checking the various parameters and the correct mastication position of the models in the articulator (FIG. 4), the dental technician then proceeds to prepare the baseplates 7 (FIGS. 5 and 6), and more specifically one for each prosthesis which is to be made. FIG. 5 illustrates the step of applying material for base plates, for example silicone or plaster paste, onto wax teeth 5. As is known, baseplates 7 associated with the corresponding models constitute the "negatives" or "prints" so that teeth 5 previously modeled in wax can be accurately obtained in resin after the wax has been removed. For this purpose baseplates 7 are removed and the wax is removed from models 1, 2, and from the individual baseplates 7, using jets of hot water, so that cavities 8 are obtained in the baseplates (FIG. 6). There follows a step in which the cavities 8 in the baseplates are filled with resin, the so-called "wedging", and this is followed by a step of polymerization of the resin, for example by stoving.

Figure 7:
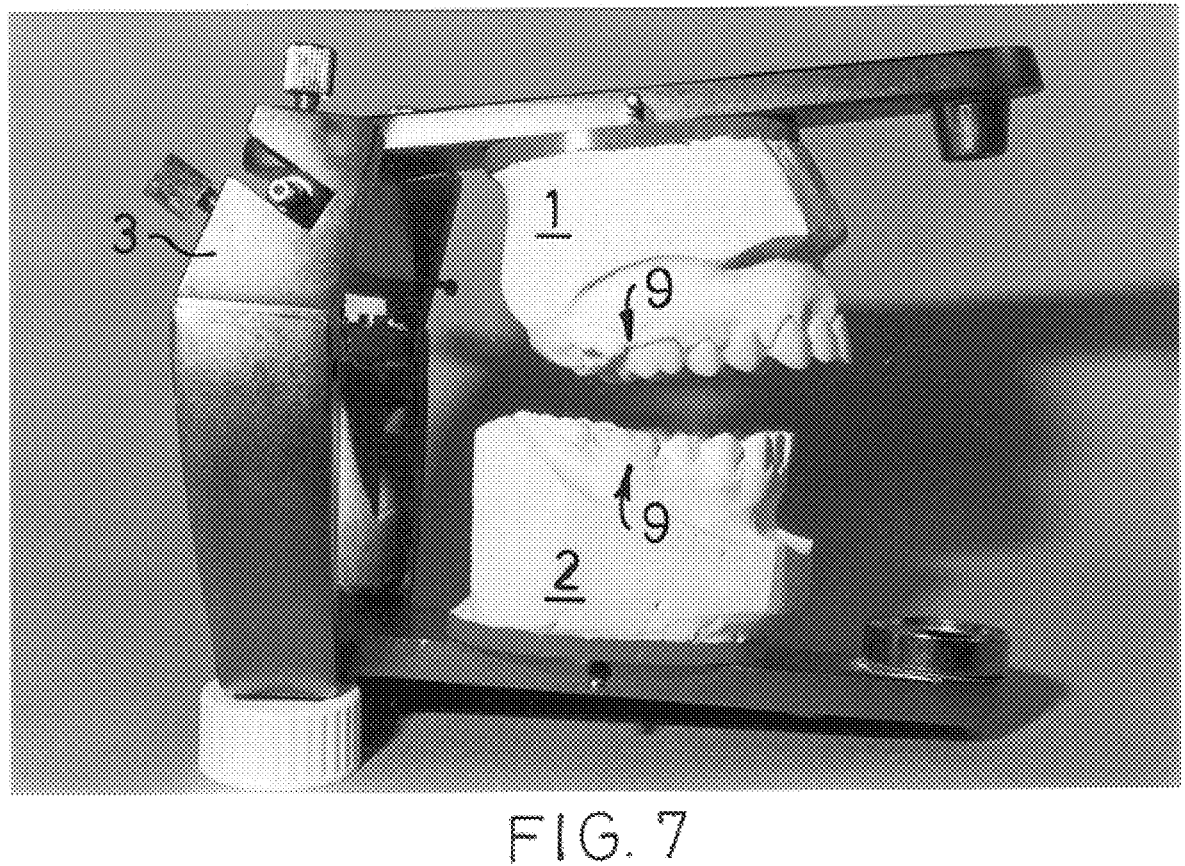
Figure 8:
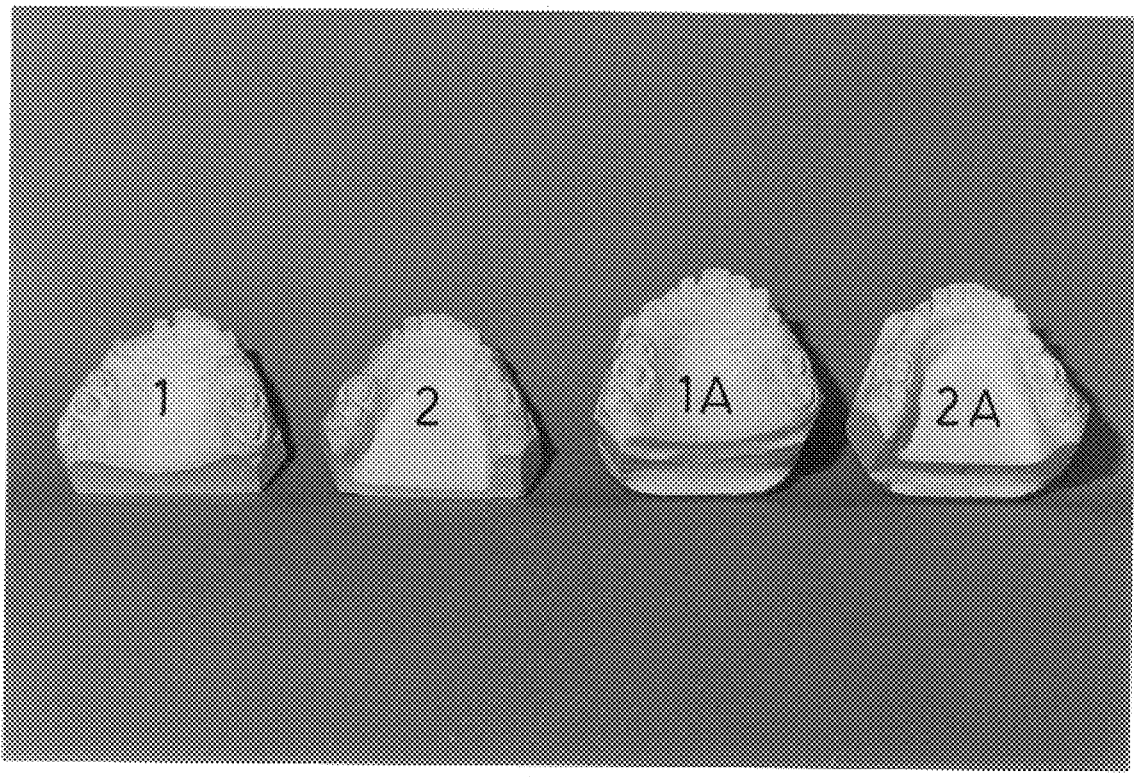
FIGS. 8 to 15 illustrate the procedure according to the invention for the production of temporary fixed prostheses and duplicates of the temporary prostheses to simplify and ensure the envisaged result for the permanent fixed prostheses, where
Figure 9:
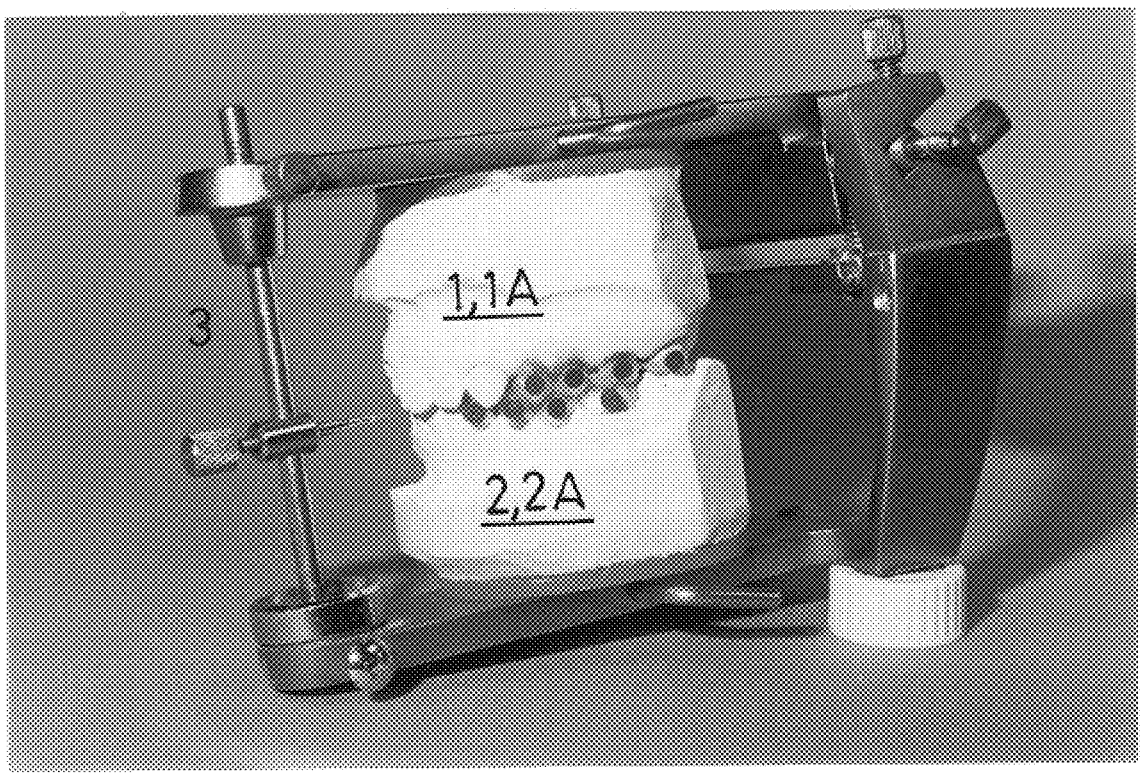
Figure 10:
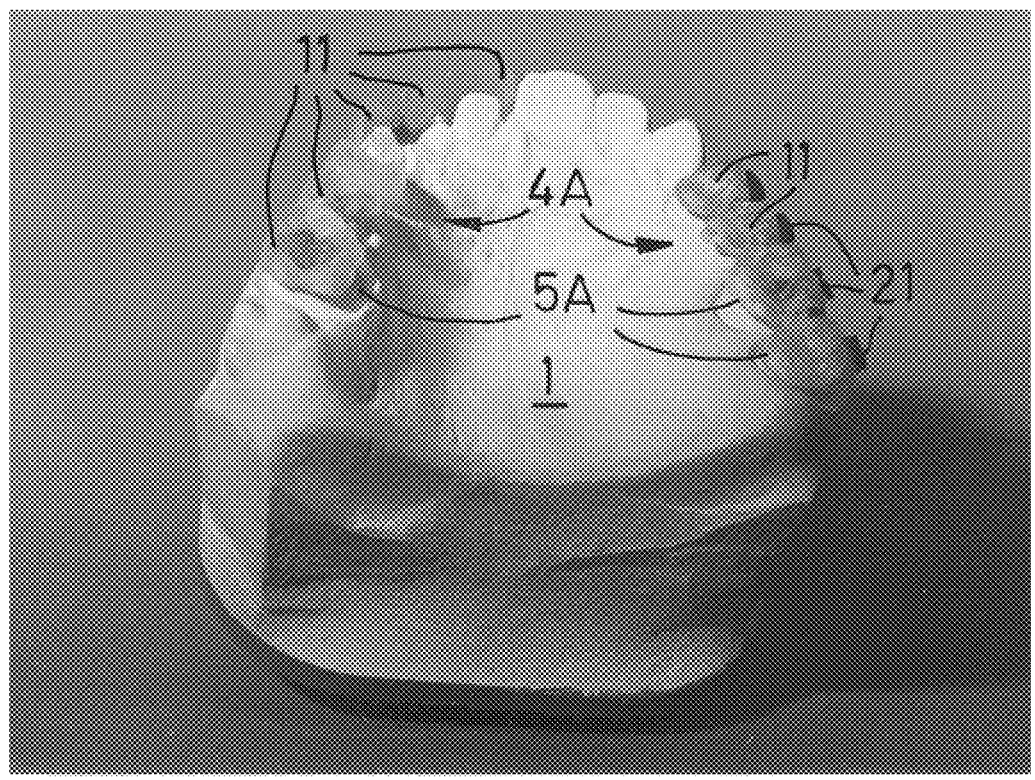
Figure 11:
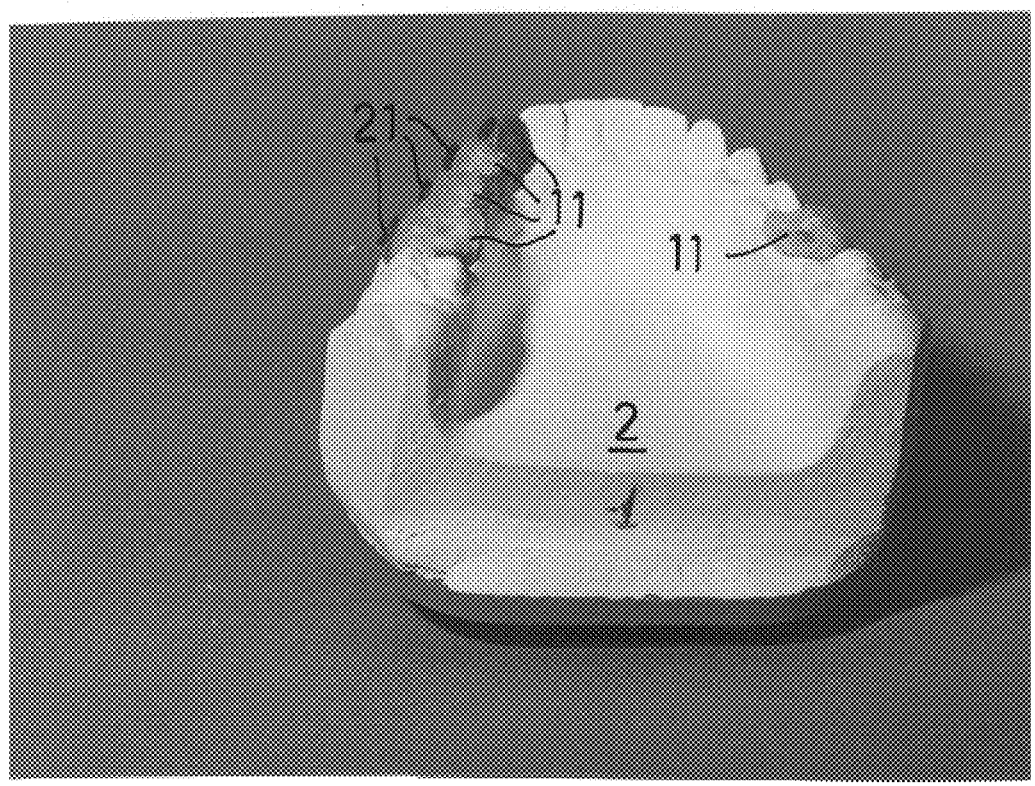

Models 1, 2 are then replaced in the articulator and the steps of checking, finishing and polishing of temporary fixed prostheses 9 are then performed (FIG. 7), and they are delivered to the dental practitioner. The latter, after fitting prostheses 9 in the patient's mouth and checking that they function satisfactorily, cements them temporarily into the patient's mouth. The procedure for producing temporary fixed dental prostheses is then completed.

When subsequently it is necessary to prepare the permanent fixed prostheses, these are made by substantially repeating the procedure mentioned above, with the corresponding disadvantages in terms of the requisite high level of manual skill in the dental technician, long working times, the accumulated experience of the dental technician and high costs.

Procedure and preformed mastication inserts according to the invention.

The procedure according to the invention can be used to reconstruct teeth pillars, missing components, implanted prostheses and so on, not only for the production of temporary fixed prostheses of resin but also, more advantageously, for the simultaneous production of duplicate temporary prostheses or "twins" which are used as an "individual patient guide" in the subsequent preparation of permanent fixed prostheses using preformed mastication inserts according to the invention.

The first two steps of the procedure according to the invention are substantially identical to the first two steps in the known procedure, that is in respect of obtaining the upper and lower models starting from the imprints obtained by the dental practitioner and positioning of the models in the articulator, together with investigation of the models in the articulator and clinical assessment from the dental treatment and dental technology points of view.

Wishing therefore to obtain the duplicate temporary prostheses mentioned above for the future production of permanent fixed prostheses, the dental technician will duplicate the models of the upper dental arch 1 and lower dental arch 2, and will also position these duplicate models 1A, 2A in a respective articulator 3. For ease of understanding the pair of first models 1, 2 will be referred to as the pair of working or master models.

Figure 16:
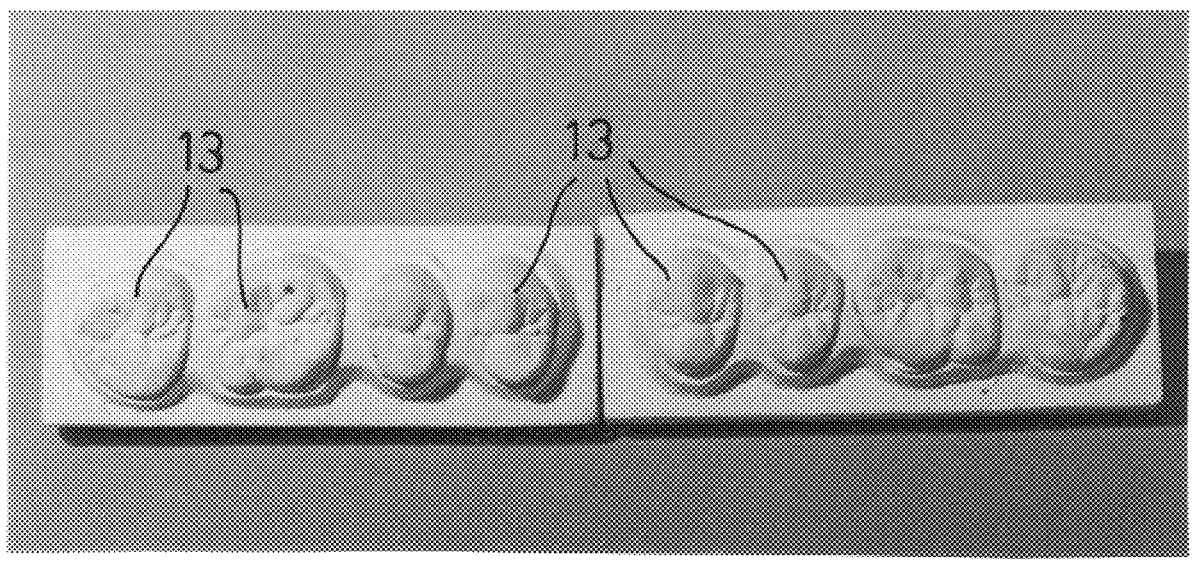
FIG. 16 illustrates two models of four different teeth respectively having cusped mastication surfaces provided to varying extents by forming in male and female molds for the production of modular preformed mastication inserts, for example of resin.
Figure 17:
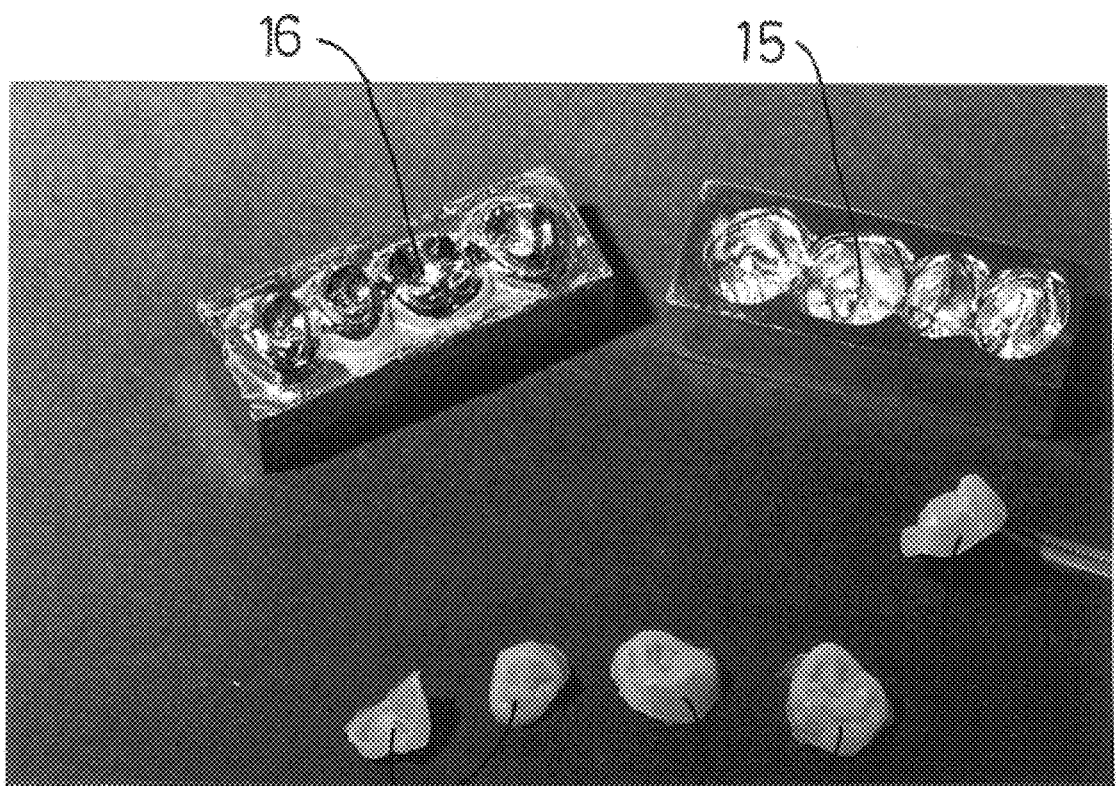
FIG. 17 shows a view of a male and female mold for obtaining single preformed mastication inserts according to the invention, with some examples of the said preformed single mastication inserts.

During the subsequent third step the dental technician, instead of making the individual teeth which have to be reconstructed from wax using the drop by drop technique and the modeling mentioned above, will merely select preformed mastication inserts 11, FIGS. 10–12, 15 and 17, from a plurality of such preformed mastication inserts 11 provided on a modular basis or in a plurality of variable shapes and sizes to allow for the different sizes of teeth existing in nature. These mastication inserts 11 already have a cusped mastication surface which has been skillfully prepared on models 13 (FIG. 16) prepared appropriately for example on teeth previously modeled in wax to obtain a male and a female mold 15, 16 (FIG. 17) to obtain the preformed mastication inserts 11, some of which are illustrated for different types of teeth in FIG. 17 as single inserts and in FIG. 15 as a single insert and a group of four inserts, respectively. Mastication inserts 11 are prepared from resin.

Satisfactory results are obtained by using an enamel mass resin of the type S15=Biodent K+B Plus® (Biodent is a registered trade mark of the DE TREY company of Wiesbaden, Germany). Inserts 11 substantially comprise a cusped mastication surface 18 (FIG. 18) and a sleeve 19 with a shaped lower edge 20. Advantageously the outer surface of inserts 11 is smooth, or polished, while the inner surface is rough in order to obtain a better bond to the resin forming the body of the tooth. Advantageously the thickness of sleeve 19 in these mastication inserts 11 is suitably shaped, more specifically in the perimetric and vertical directions.

The dental technician therefore has available a plurality of such preformed mastication inserts 11 which constitute a modular set or series for a particular type of tooth, for example a premolar, molar and so on, in which different shapes of cusp and different sizes are advantageously provided so that having regard to the patient's dentition the dental technician will have no problems in rapidly finding the most suitable mastication inserts 11 for the individual teeth which have to be reconstructed.

This being the case, the dental technician, having available to him a series of preformed mastication inserts 11, will immediately be able to choose the most suitable individual mastication inserts, making an immediate assessment of the balance between shape, function and individual problems. When an individual mastication insert 11 has been selected in this way for each tooth which has to be formed, the dental technician will fit the mastication insert 11 into its "natural position", using a few drops of wax to fix it on model 1 or 2. When the individual mastication insert 11 is fixed in this way the dental technician will complete the "body" of tooth 5A, FIG. 10, quickly applying further wax which he will easily model so as to obtain the corresponding temporary fixed prosthesis 4A, tooth by tooth on models 1 and 2, formed of tooth bodies 5A of wax and corresponding mastication inserts 11. The drastic saving in time and the modest requirement for modeling skill required from the dental technician, who can therefore save time and improve the quality of his own work, is therefore obvious.

Figure 12:
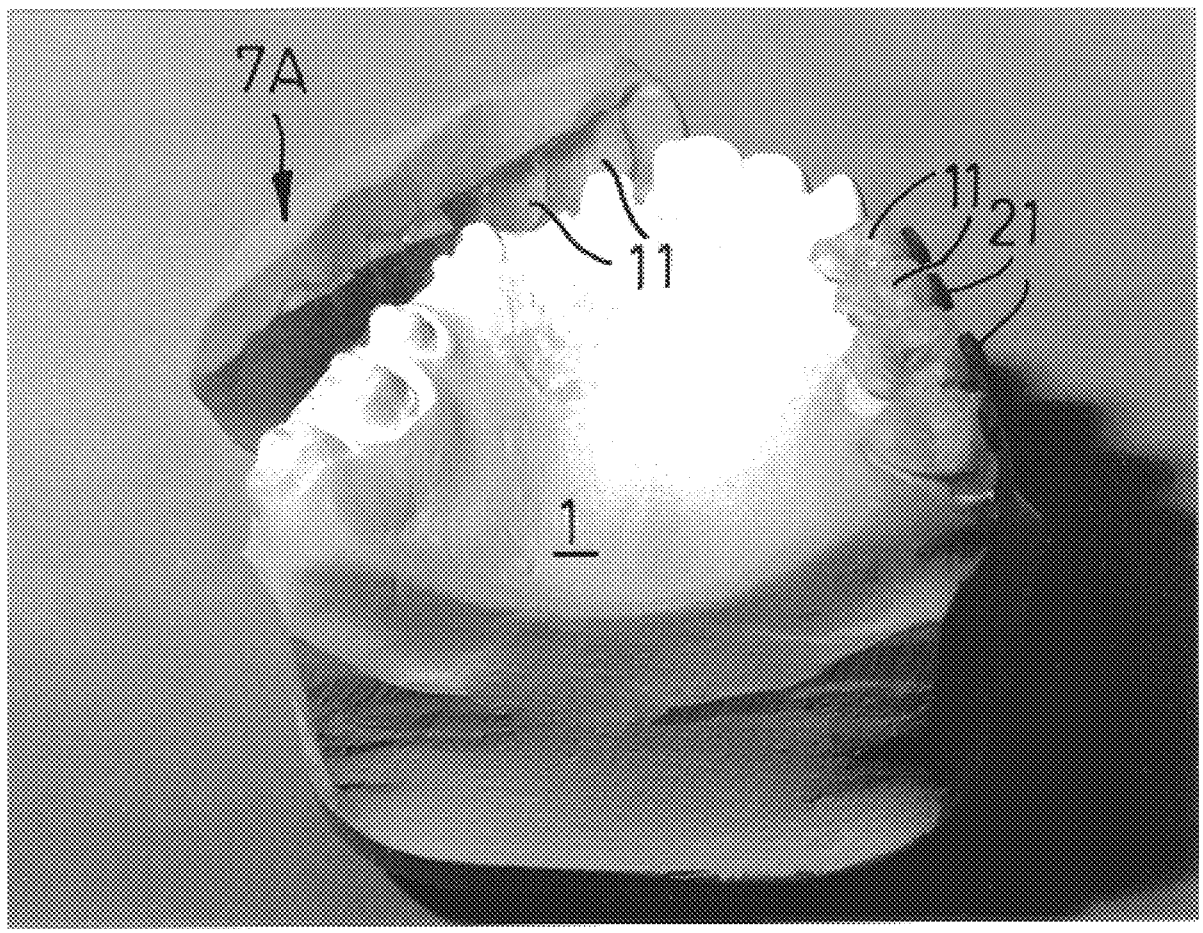
Figure 13:
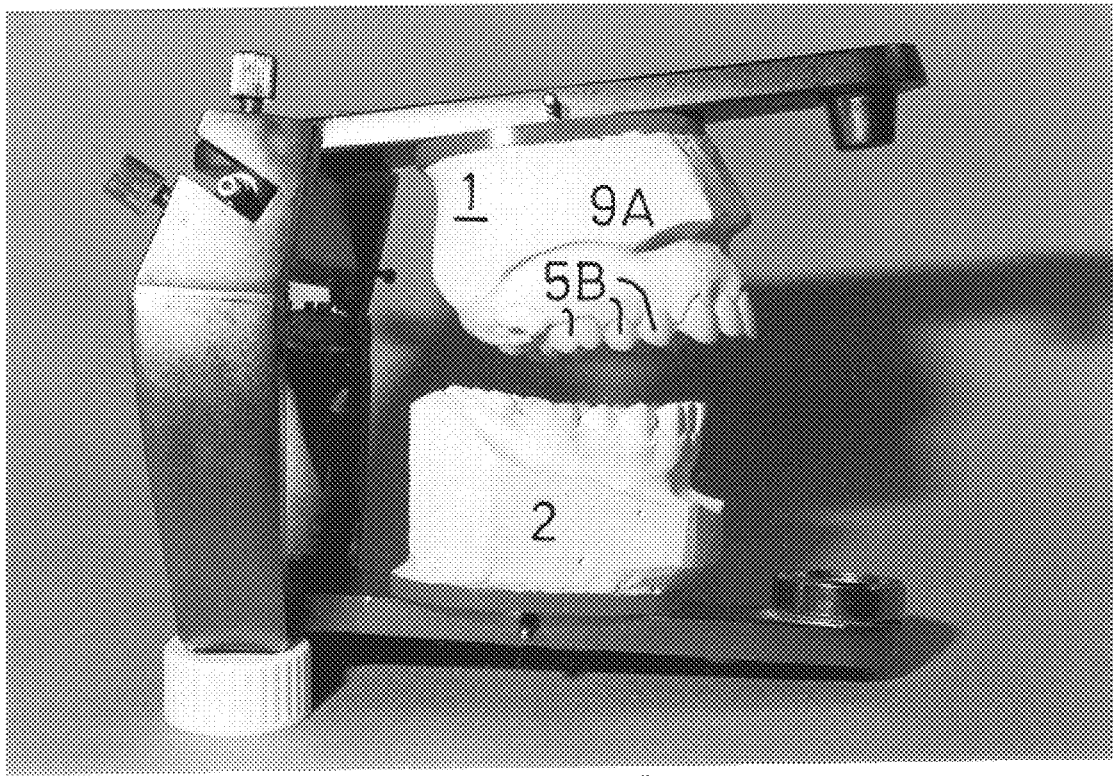
Figure 14:
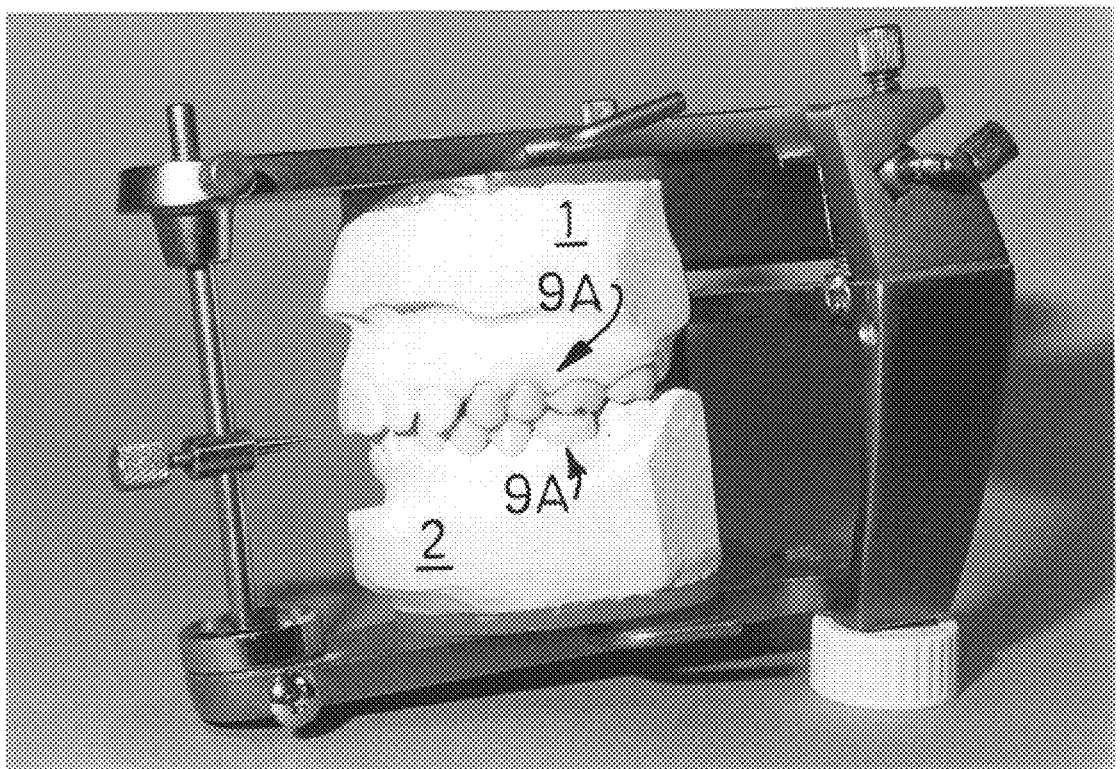
Figure 15:
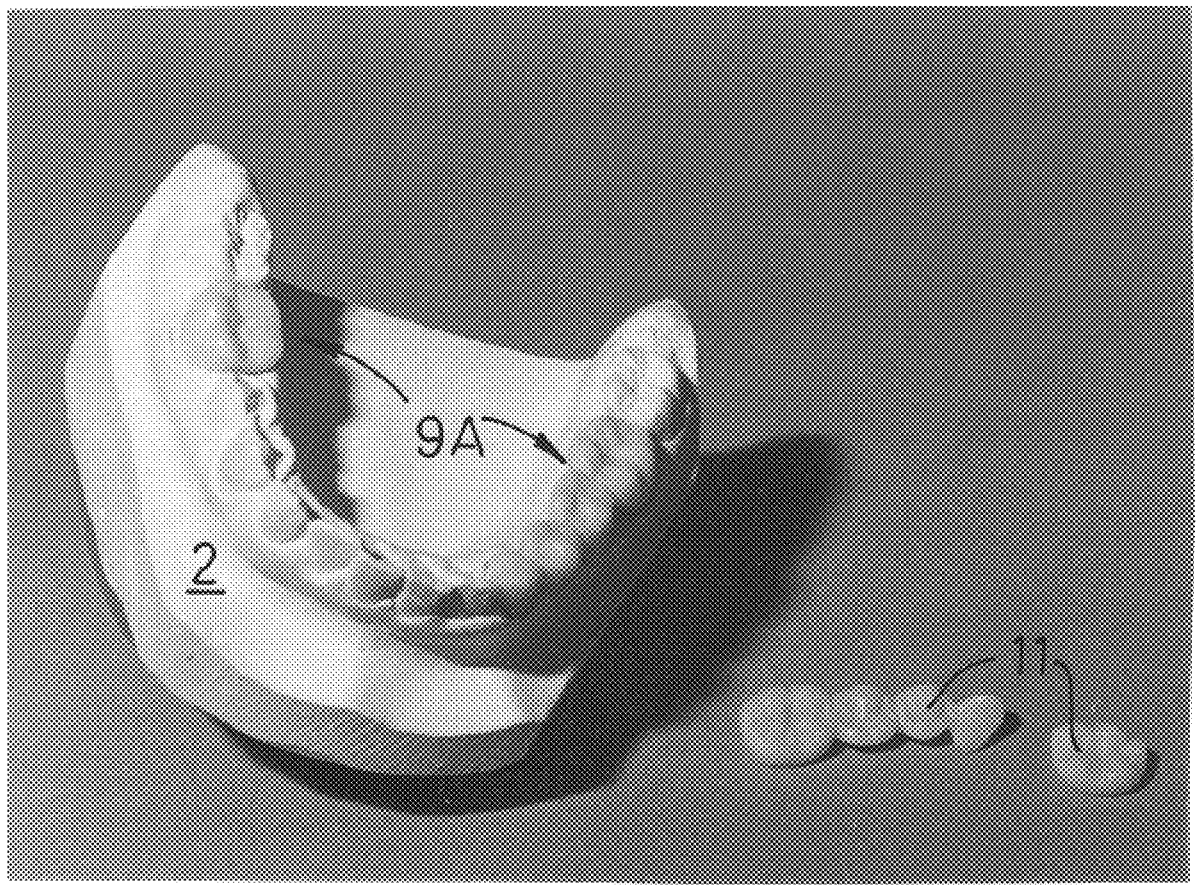

After checking various parameters, for example correct occlusion between the constructed tooth and the associated upper or lower tooth, baseplates 7A are prepared in the normal way (FIG. 12). As far as baseplates 7A themselves are concerned, after being separated from the model and after the wax has been removed from the model and the individual baseplates using jets of hot water, the baseplates 7A will firmly support in the bottom of the cavities 8 thereof the individual preformed mastication inserts 11 which will form the mastication zone of the individual teeth 5B of the finished temporary prostheses 9A (FIG. 13). The means whereby they are held or retained will be discussed in detail below.

After baseplates 7A have been obtained with the corresponding cavities 8 supporting mastication inserts 11 and cleaned of wax, resin is placed or "wedged" into these cavities 8 which incorporate in the bottom thereof the secured mastication inserts 11 mentioned which will form an integral part of the individual temporary resin teeth 5B, FIG. 13.

It is pointed out here that in accordance with the invention, and also desiring to create permanent fixed prostheses, the dental technician will use baseplates 7A twice. More specifically the first "wedging" will, as mentioned above, be used to obtain the temporary fixed prostheses incorporating mastication inserts 11.

With the second wedging, using the same baseplates 7A, the dental technician will obtain a "twin" replica or copy which is absolutely identical to the temporary fixed prostheses, and more specifically will use these baseplates first on master models 1, 2 to obtain the temporary fixed prostheses and then on duplicate models 1A, 2A for the duplicate or "twin" fixed prostheses.

After the usual polymerization, the temporary fixed and twin prostheses will be checked and finished, the temporary fixed prostheses being polished or subsequently temporarily cemented into the patient's mouth by the dental practitioner, after making such checks as are necessary.

Subsequently, after the dental practitioner has established that it is appropriate for the patient to receive the permanent fixed prostheses according to the invention, after the temporary prostheses have been removed from the patient the dental practitioner will then make a record of the impressions and occlusion. During this step the duplicate or "twin" prostheses are used, and these, filled with impression material, are placed in the patient's mouth and used to obtain the occlusion, the laterals, the masticatory functions and the final impression. Having then received the impressions from the dental practitioner, the dental technician develops and adjusts the duplicate prostheses inserted in new permanent models (not illustrated) which are then mounted in the articulator.

Without removing the "twin" prostheses from the models, the baseplates are then prepared. The permanent fixed prostheses are then obtained from the baseplates using the known steps in preparation, before they are fixed in the patient's mouth by the dental practitioner.

Also, in accordance with the invention, using the baseplates for the permanent prostheses it is also possible, advantageously, to obtain crowns and metal structures, for example of gold, or similar components. As mentioned above, preformed mastication inserts 11 can be made of resin by any suitable technique, for example by molding using a male and female mold, 15, 16 respectively. Such molds can also be provided for manufacturing one-piece groups of two or more single mastication inserts.

Figure 18:
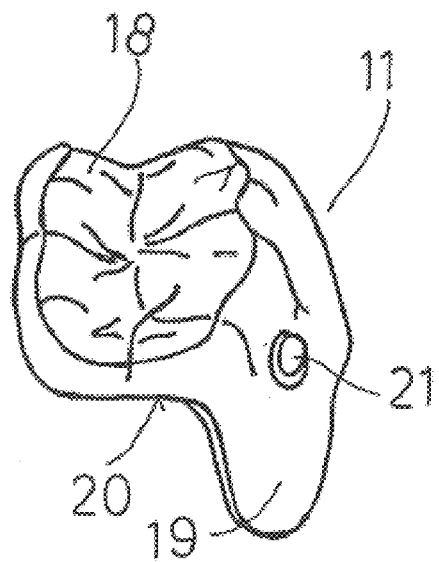
FIG. 18 shows a mastication insert according to the invention on an enlarged scale.

In order to aid retention of the said preformed mastication inserts 11 in the baseplates, the inserts have outer retaining means 21 on sleeve 19 which are formed integrally in the course of molding, in the shape of pin, boss, mushroom head or similar bodies, or as removable bodies which can be adhesively bonded to the sleeve of the inserts, FIG. 18.

In the "twin" prostheses the retention means, which are not illustrated, are obtained integrally from the cavities of retaining means 21 of the temporary prostheses, cavities which are subsequently filled with resin.

The shape of sleeve 19, or its free perimetric edge 20, is constructed so as to ensure both the necessary mobility in space which has to be allowed mastication inserts 11 so that they can be correctly positioned to engage with the associated upper or lower tooth, and also to ensure satisfactory anchorage of the resin forming the prosthesis and a satisfactory color match between the mastication inserts 11 and the underlying resin.

From the above description it will be seen that the objects which are to be accomplished by the invention are effectively resolved by the procedures and the preformed mastication inserts according to the invention, and the advantages mentioned above are obtained.

In practice the procedure for implementing the invention, both for the production of individual temporary fixed prostheses and also for the subsequent production of permanent fixed prostheses, can from time to time include steps which differ from those indicated, for example on the basis of the materials used, the types of reinforcement in the individual prostheses, and so on, although these variants all lie within the scope of the protection of this invention.

The materials used and the techniques for the production of preformed single mastication inserts or one-piece groups of mastication inserts as well as the number of mastication inserts or insert groups in the series or sets of said preformed mastication inserts provided as a working key for dental technicians and dental practitioners can be varied at will without departing from the central characteristics thereof. Temporary fixed prostheses or permanent fixed prostheses produced in accordance with the teaching of this invention likewise fall within the scope of the present invention.

The present examples and embodiments, therefore, are to be considered in all respects as illustrative and not restrictive, and the invention is not to be limited to the details given herein.

We claim:

1. A procedure for preparing a dental prosthesis made of resin, the procedure comprising the steps of:

making upper and lower working models of a patient's upper and lower teeth;

mounting the upper and lower working models in an articulator for defining features of the dental prosthesis;

selecting preformed indeformably hard resin mastication inserts from a plurality of such inserts, each of the mastication inserts having means for retention in a baseplate;

forming rough wax tooth bodies on the working models;

attaching the selected mastication inserts to the respective wax tooth bodies;

adding and shaping wax lingual and palatal cervical zones for the respective wax tooth bodies and mastication inserts;

preparing baseplates by applying a baseplate material to the working models around the mastication inserts and shaped wax tooth bodies, the mastication inserts being retained in the respective baseplates by the respective retaining means;

after removing the wax tooth bodies and with the mastication inserts retained in the baseplates, wedging a resin between the mastication inserts and the working models;

polymerizing the wedged resin; and removing the retaining means from the mastication inserts that are attached to the polymerized resin.

2. A procedure for preparing temporary and permanent dental prostheses made of resin, the procedure comprising the steps of:

making upper and lower working models of a patient's upper and lower teeth;

making copies of the working models;

mounting the upper and lower working models and the copies thereof in respective articulators for defining features of the dental prostheses;

selecting preformed indeformably hard resin mastication inserts from a plurality of such inserts, each of the mastication inserts having means for retention in a baseplate;

forming rough wax tooth bodies on the working models;

attaching the selected mastication inserts to the respective wax tooth bodies on the working models;

adding and shaping wax lingual and palatal cervical zones for the respective wax tooth bodies on the working models;

preparing baseplates for the temporary prosthesis by applying a baseplate material to the working models around the mastication inserts and shaped wax tooth bodies, the mastication inserts being retained in the respective baseplates by the respective retaining means;

after removing the wax tooth bodies and with the mastication inserts retained in the baseplates, wedging a resin between the mastication inserts and the working models;

polymerizing the wedged resin;

removing the retaining means from the mastication inserts that are attached to the polymerized resin, whereby the temporary prosthesis is formed;

inserting the temporary prosthesis into the copies of the working models;

preparing further baseplates using the temporary prosthesis in the copies of the working models;

after removing the temporary prostheses, wedging a resin between the further baseplates and the copies of the working models to form the permanent prosthesis.

3. The procedure of claim 2, further comprising the step of inserting further mastication inserts into correspondingly shaped cavities in the further baseplates, and wherein the resin is wedged between the further mastication inserts and the copies of the working models.

4. The procedure of claim 2, further comprising the step of making a crown using one of the further baseplates.

5. A preformed mastication insert for a dental prosthesis, comprising a body of substantially transparent, hard, thermo-indeformable material, a cusped mastication surface, and a sleeve depending from said mastication surface.

6. The insert of claim 5, further comprising a removable projection projecting from said sleeve for anchoring said insert in a baseplate.

7. The insert of claim 5, wherein said sleeve has a varying thickness for obtaining a desired chromatic effect.

8. The insert of claim 5, wherein said mastication surface has a varying thickness for obtaining a desired chromatic effect.

9. The insert of claim 5, wherein said insert comprises a smooth exterior surface and a rough interior surface.

10. Plural mastication inserts according to claim 5 that are bonded together.

* * * * *